(12) United States Patent
Doan et al.

(10) Patent No.: US 7,139,000 B2
(45) Date of Patent: Nov. 21, 2006

(54) METHOD, SYSTEM AND COMPUTER PRODUCT FOR DISPLAYING AXIAL IMAGES

(75) Inventors: William D. Doan, Pewaukee, WI (US); Robert Harry Armstrong, Waukesha, WI (US); Brian Christopher Frake, Waukesha, WI (US); Toan T. Le, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 534 days.

(21) Appl. No.: 10/063,786

(22) Filed: May 13, 2002

(65) Prior Publication Data

US 2003/0210254 A1 Nov. 13, 2003

(51) Int. Cl.
*G06T 17/00* (2006.01)
*A61B 6/00* (2006.01)

(52) U.S. Cl. .............................. 345/424; 378/4; 378/8; 378/15; 378/19

(58) Field of Classification Search ................ 345/424; 378/4–19
See application file for complete search history.

(56) References Cited

U.S. PATENT DOCUMENTS

| | | | |
|---|---|---|---|
| 5,732,118 A | 3/1998 | Hsieh ........................... | 378/19 |
| 5,825,842 A * | 10/1998 | Taguchi ........................ | 378/15 |
| 5,974,110 A | 10/1999 | Hu ............................... | 378/19 |
| 5,986,662 A * | 11/1999 | Argiro et al. ................ | 345/424 |
| 6,023,494 A | 2/2000 | Senzig et al. ................... | 378/4 |
| 6,061,420 A | 5/2000 | Strong et al. ................... | 378/4 |
| 6,081,576 A | 6/2000 | Schanen et al. .............. | 378/19 |
| 6,141,398 A * | 10/2000 | He et al. ........................ | 378/4 |
| 6,198,791 B1 | 3/2001 | He et al. ....................... | 378/19 |
| 6,275,562 B1 | 8/2001 | He et al. ....................... | 378/19 |
| 6,404,844 B1 * | 6/2002 | Horiuchi et al. ............... | 378/8 |
| 6,584,166 B1 * | 6/2003 | Taguchi ....................... | 378/19 |
| 2003/0123603 A1* | 7/2003 | Suzuki .......................... | 378/4 |

* cited by examiner

*Primary Examiner*—Kee M. Tung
*Assistant Examiner*—Jin-Cheng Wang
(74) *Attorney, Agent, or Firm*—Cantor Colburn LLP

(57) ABSTRACT

A method for displaying axial images that comprises receiving a reconstructed axial image. The reconstructed axial image includes a pre-selected number of completed reconstructed slices, a slice thickness and an interval value. A reformatted axial image is created in response to the reconstructed axial image. The creation of a reformatted axial image includes modifying the slice thickness in response to user slice thickness input and updating the interval value in response to user interval value input. The reformatted axial image is displayed in response to user display input.

16 Claims, 2 Drawing Sheets

METHOD, SYSTEM AND COMPUTER PRODUCT FOR DISPLAYING AXIAL IMAGES

BACKGROUND OF INVENTION

The present disclosure relates generally to a method for displaying axial images and in particular, to a method for displaying axial images at varying slice thicknesses and interval values.

A medical imaging configuration, such as a computed tomography (CT) system can include an x-ray source that projects a fan-shaped beam which is collimated to lie within an X-Y plane of a Cartesian coordinate system and generally referred to as the "imaging plane." The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements are acquired separately to produce a transmission profile.

CT systems can also include the x-ray source and the detector array being rotated with a gantry within the imaging plane and around the object to be imaged so that the angle at which the x-ray beam intersects the object constantly changes. A group of x-ray attenuation measurements i.e., projection data, from the detector array at one gantry angle is referred to as a "view". A "scan" of the object comprises a set of views made at different gantry angles during one revolution of the x-ray source and detector.

In an axial scan, projection data is processed to construct an image that corresponds to a two dimensional slice taken through the object. One method for reconstructing an image from a set of projection data is referred to as the filtered back projection technique. This process converts the attenuation numbers from a scan into integers called "computed tomography numbers" or "Hounsfield units", which are used to control the brightness of a corresponding pixel on a cathode ray tube display.

Slice thickness directly affects image resolution and scan efficiency. Typically, the optimal slice thickness will vary depending upon a variety of factors including the type of procedure being performed. Smaller slice thicknesses provide a more detailed image resolution than larger slice thicknesses. However, larger slice thicknesses are more efficient than small slice thicknesses since more of the region is scanned with a large slice thickness in a shorter period of time and larger slice thicknesses are easier to page through in order to find the slice that contains the area of interest. Typically, an operator selects a slice thickness prior to a scan to optimize scan efficiency and image quality based on a variety of factors including the type of procedure being performed.

SUMMARY OF INVENTION

One aspect of the invention is a method for displaying axial images that includes receiving a reconstructed axial image. The reconstructed axial image includes a pre-selected number of completed reconstructed slices, a slice thickness and an interval value. A reformatted axial image is created in response to the reconstructed axial image. The creation of a reformatted axial image includes modifying the slice thickness in response to user slice thickness input and updating the interval value in response to user interval value input. The reformatted axial image is displayed in response to user display input.

Another aspect of the invention is a method for displaying axial images that includes receiving a reconstructed axial image. The reconstructed axial image includes a slice thickness and an interval value. A reformatted axial image is created in response to the reconstructed axial image. The creation of a reformatted axial image includes modifying the slice thickness in response to user slice thickness input and updating the interval value in response to user interval value input. The user interval value input includes an explicit value for the interval value. The reformatted axial image is displayed in response to user display input.

Another aspect of the invention is a computer program product for displaying axial images. The computer program product includes a storage medium readable by a processing circuit. The storage medium stores instructions for execution by the processing circuit including an instruction to receive a reconstructed axial image. The reconstructed axial image includes a pre-selected number of completed reconstructed slices, a slice thickness and an interval value. A reformatted axial image is created in response to the reconstructed axial image. The creation of a reformatted axial image includes modifying the slice thickness in response to user slice thickness input and updating the interval value in response to user interval value input. The reformatted axial image is displayed in response to user display input.

A further aspect of the invention is a computer program product for displaying axial images. The computer program product includes a storage medium readable by a processing circuit. The storage medium stores instructions for execution by the processing circuit including an instruction to receive a reconstructed axial image. The reconstructed axial image includes a slice thickness and an interval value. A reformatted axial image is created in response to the reconstructed axial image. The creation of a reformatted axial image includes modifying the slice thickness in response to user slice thickness input and updating the interval value in response to user interval value input. The user interval value input includes an explicit value for the interval value. The reformatted axial image is displayed in response to user display input.

A further aspect of the invention is a system for displaying axial images. The system comprises an image database that includes a reconstructed axial image, a workstation and a viewing processor. The viewing processor is in communication with the image database and the workstation. The viewing processor includes viewing application software to implement a method for displaying the axial images. A reconstructed axial image is received and it includes a pre-selected number of completed reconstructed slices, a slice thickness and an interval value. A reformatted axial image is created in response to the reconstructed axial image. The creation of a reformatted axial image includes modifying the slice thickness in response to user slice thickness input and updating the interval value in response to user interval value input. The reformatted axial image is displayed in response to user display input.

Further aspects of the invention are disclosed herein. The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures.

DETAILED DESCRIPTION

An embodiment of the present invention allows a user to display axial images at slice thicknesses and interval values other than what was natively prescribed. The display of the axial image may occur while scanning and reconstruction of the image is in process or it may occur after the scanning and reconstruction has been completed. In an exemplary embodiment, reconstructed images are summed using a weighted algorithm allowing the user to cine through a large image dataset. In an exemplary embodiment of the present invention, the user can select the visualized slice thickness and interval value.

Figure 1:
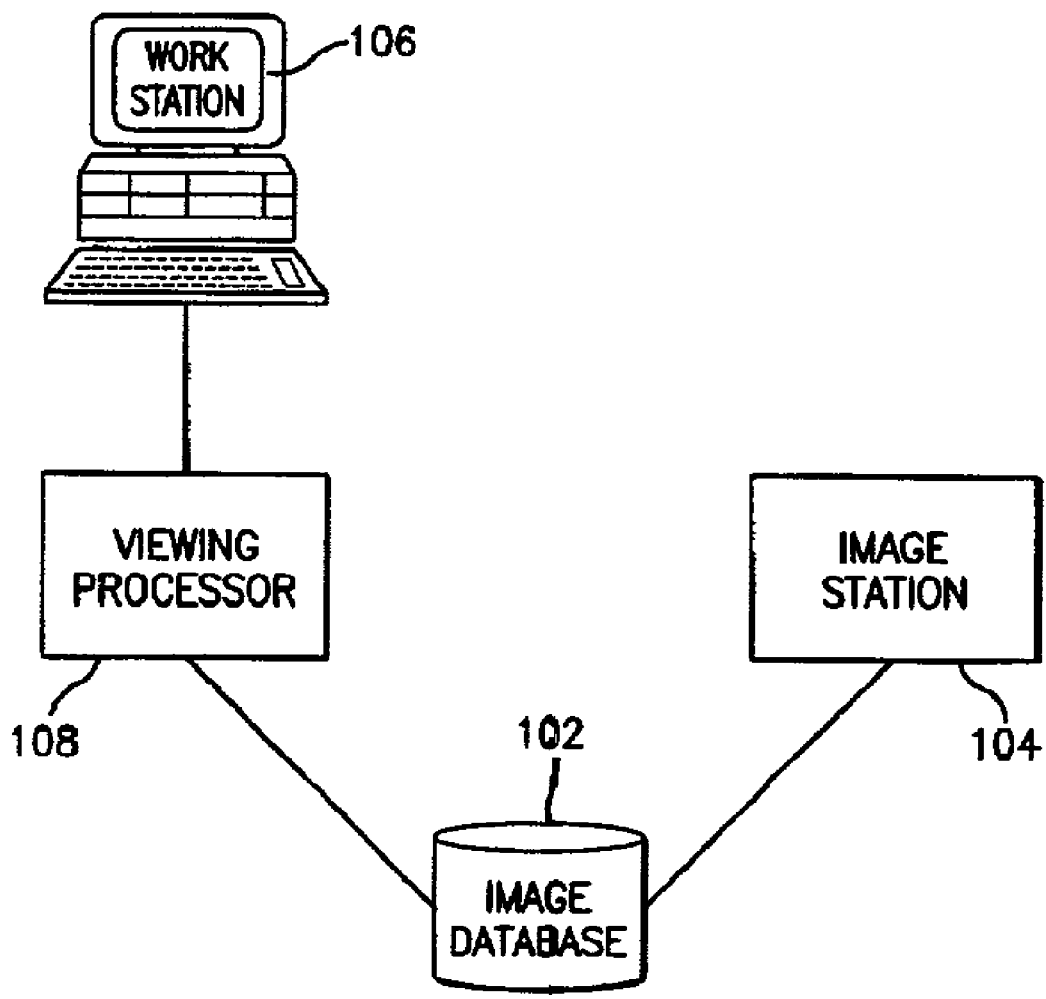
FIG. 1 is a block diagram of an exemplary system for displaying axial images.

FIG. 1 is a block diagram of an exemplary system for displaying axial images. The system includes an image station 104 for creating axial images. In an exemplary embodiment, the image station 104 is a computed tomography (CT) device but any imaging device that can create axial images may be used. The image station 104 creates reconstructed axial images that are stored in the image database 102. The system also includes a viewing processor 108 to run the viewing application software. In an exemplary embodiment, the image database 102 is connected (e.g., directly, via a network) to the viewing processor 108 and the image station 104. The image database 102 may be implemented in a variety of devices for storing electronic information (e.g., a file transfer protocol server) and in a variety of database formats (e.g., relational). It is understood that the image database 102 may be implemented using memory contained in the viewing processor 108 or memory contained in the image station 104. Alternatively, the image database 102 may be a separate physical device. The system also includes a workstation 106 that can be used as a viewport for the viewing application software. The workstation 106 is connected to the viewing processor 108. In an exemplary embodiment, the workstation 106 is a personal computer and is shared by both the image station 104 and the viewing processor 108. If the workstation 106 is implemented with a personal computer, the processing described herein may be shared by the viewing processor 108 and the workstation 106.

A variety of system configurations are possible. For example, the viewing processor 108, image database 102, image station 104 and workstation 106 could all be physically located on the same computer processor or they could be located on four separate computer processors. In addition, the viewing processor 108, image database 102, image station 104 and workstation 106 could be located in the same geographic location and directly connected to each other or they could be located in four different geographic locations and connected to each other through a network (e.g., local area network (LAN), intranet, Internet). An exemplary embodiment includes the viewing processor 108 being a separate physical device from the image station 104. It also includes both the image station 104 and the viewing processor 108 having access to data stored in the image database 102 which is located on a separate physical device. In addition, the workstation 106 is connected to the viewing processor 108. In this exemplary embodiment, a first configuration can include all four components being physically located in the same geographic location and connected directly or through a LAN. A second option can include having the viewing processor 108 and the workstation 106 located in a separate geographic location from the image database 102 and image station 104. Access to the image database 102 by the viewing processor 108 could be over a network. This second configuration would allow the operator of the viewing processor 108 to be in one geographic location and the patient being scanned in another geographic location. A third configuration can include having the workstation 106 located in a separate geographic location from the viewing processor 108, the image database 102 and the image station 104. This would allow the operator of the workstation 106 to be in one geographic location, the patient being scanned in another geographic location, and the viewing application software in a third geographic location. A variety of additional configurations are possible based on user requirements.

Figure 2:
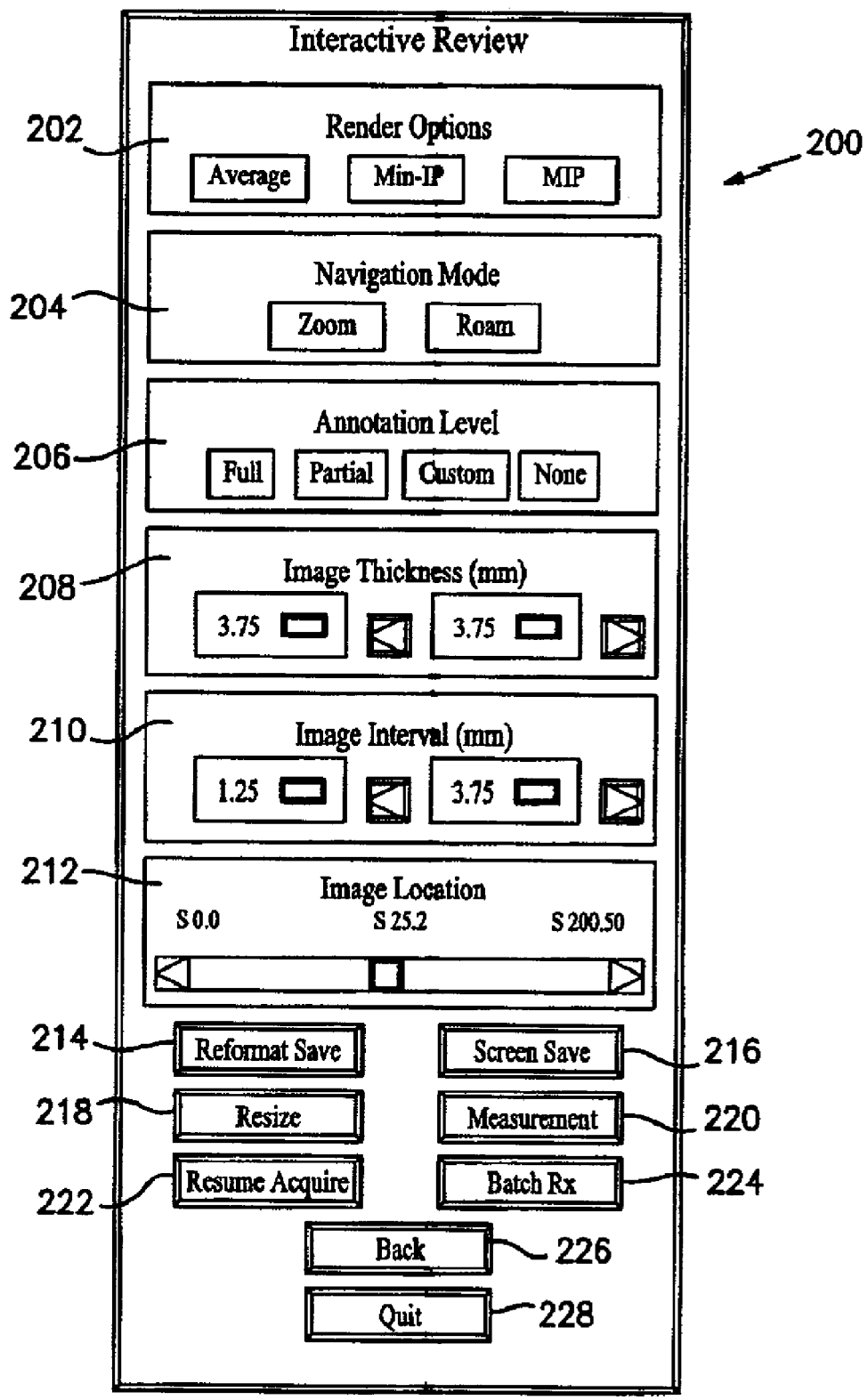
FIG. 2 is an exemplary embodiment of an interactive review screen for displaying axial images.

FIG. 2 is an exemplary embodiment of a interactive review screen 200 to display axial images using viewing application software running on the viewing processor 108. The viewing application software can be executed through the interactive review screen 200 before the image reconstruction has been completed for the whole image being captured by the image station 104. In an exemplary embodiment, once four slices have been reconstructed and stored in the image database 102, the viewing application software can begin displaying and modifying the reconstructed axial image, and creating a reformatted axial image. The number of slices that must be reconstructed before the viewing application software can begin display and modification is a user selected value. The user can select options on the interactive review screen 200, referred to as user display input, and make changes to the way that an image is displayed on the viewport in a real-time on-line manner. The interactive review screen 200 is displayed on the viewport on the workstation 106. Render options 202 include average intensity pixel, minimum intensity pixel and maximum intensity pixel. The pixel display will respond to the level of the intensity selected by the user. In an exemplary embodiment, rendering is performed using an averaging method. Navigation mode options 204 include zoom and roam. In an exemplary embodiment, zoom is the default navigation mode when the viewing application session is started. To change the navigation mode, the user can select the appropriate option and use the right mouse button on the viewport to adjust the zoom/roam. The user interface screen also includes four annotation options 206: full, partial, custom and none. In an exemplary embodiment, full annotation includes: current acquisition status, current reformat location, current reformat thickness and render mode option, date, patient name, and hospital name. To change the annotation level a user can select the appropriate option and the selected annotation level will be shown on the viewport on the current display image.

Referring to FIG. 2, users will have the ability to adjust the image thickness using the image thickness control 208, resulting in input to the viewing application software referred to as user slice thickness input. In an exemplary embodiment, several controls exist to adjust the image thickness. The user can type in an explicit thickness in a text field. The thickness value is a multiple factor of the acquired thickness used during the original axial imaging. Minimum thickness is the acquired thickness, and maximum thickness is determined based on the performance measurement of the reformat engine. The values on the thickness pull-down menu are updated accordingly. Other controls that can be used to adjust the image thickness are the left arrow button that decreases the current thickness value by a pre-selected increment (e.g., one half of a millimeter, one quarter of a millimeter) and a right arrow button that increases the current thickness value by a pre-selected increment (e.g., one half of a millimeter, one quarter of a millimeter). In addition, an exemplary embodiment also includes a drop down menu with pre-selected thicknesses (e.g., 1.25, 2.50, 3.75, 5.00, 7.50, 10.0). In an exemplary embodiment, the user will not be able to choose a pre-selected thicknesses on the pull down menu that is less than the acquired thickness. In response to a user selecting a thickness from the drop down menu, the thickness text field is updated to correspond to the selected thickness and the reformatted image is displayed on the viewport. Any reformatting engine known in the art can be utilized to create the reformatted image for display.

The image interval control 210 operates in a manner similar to the image thickness control 208. In an exemplary embodiment, the image interval will default to the selected thickness value when the user changes the image thickness value. Referring to FIG. 2, users will have the ability to adjust the image interval using the image interval control 210, resulting in input to the viewing application software referred to as user interval value input. In an exemplary embodiment, several controls exist to adjust the image interval. First, the user can type in an explicit interval value in a text field. Other controls that can be used to adjust the image interval are the left arrow button that decreases the current interval value by a pre-selected increment (e.g., one half of a millimeter, one quarter of a millimeter) and a right arrow button that increases the current interval value by a pre-selected increment (e.g. one half of a millimeter, one quarter of a millimeter). In addition, an exemplary embodiment also includes a drop down menu with pre-selected intervals (e.g. 1.25, 2.50, 3.75, 5.00, 7.50, 10.0). In response to a user selecting an interval value from the drop down menu, the interval value text field is updated to correspond to the selected interval and the reformatted image is displayed on the viewport. Any reformatting engine known in the art can be utilized to create the reformatted image for display.

Adjusting the image thickness and image interval allows the user to get different incremental views of a reconstructed image that is displayed on the viewport. The reformatting engine uses the image thickness and image interval to determine what to display on the viewport. The image interval defines the distance between the center of each reformatted slice. If the interval is equal to two, there will be two millimeters between the center of each slice in the reformatted image. For example, the image may have been scanned in at an acquired thickness of one millimeter and contain ten slices (a very low number for purposes of this example only). The user may request a view of the image at a slice thickness of four and an interval of two. In response to the user request, the viewport will display an image with slices containing the following start and end points relative to the original ten slices: starting at zero and ending at four; starting at two and ending at six; starting at four and ending at eight; and starting at six and ending at ten. The user can then page through the reformatted image data on the viewport four slices at a time at an increment of two.

FIG. 2 also depicts an image location control 212 as part of the user display input. In an exemplary embodiment, several controls can be used to change the image location. A scroll bar slider control is used to move from superior to inferior or vice versa. The left arrow button control can be selected to change the image location toward inferior by the amount that is specified in the image interval control 210. The right arrow button control can be selected to change the image location toward superior by the amount specified in the image interval control 210. In addition, the center label in the image location control 212 indicates the current location for the current image and the left/right labels specify the scan ranges for images that are constructed when the user enters the interactive review screen 200.

The reformat save button 214, another user display input, depicted in FIG. 2 allows the user to save the current image in the viewport in the image database 102 in a pre-selected format (e.g., DICOM) and using a pre-selected naming convention. In an exemplary embodiment, the reformat save button 214 causes the reformatted image to be stored in a DICOM reformat format. The screen save button 216, also a user display input, allows the user to save the current image in the viewport as a secondary capture image in the image database 102. In an exemplary embodiment, the screen save button 216 causes the reformatted image to be stored in a secondary capture DICOM format. The resize button 218, another user display input, allows a user to switch the viewport display size from one value to another (e.g., from 512×512 to 768×768 and vice-versa). The measurement button 220 invokes an application that includes a screen with measurement tools. The measurement screen includes a variety of tools to take measurements of the image, including squares, angles, and circles. In an exemplary embodiment, the measurement screen is the same screen used by the image station 104 during the scanning process. The ability to invoke an application program is also used by the resume acquire button 222. The resume acquire button 222 allows the user to leave the interactive review screen 200 and resume the acquire mode on the image station 104 to continue to accept new images into the image database 102. When the user selects the resume acquire button 222, the interactive review screen 200 is exited and the acquire system screen associated with the image station 104 is displayed on the viewport. In an exemplary embodiment, a button labeled "enter viewing application" will be displayed on the acquire system screen to allow the user to reenter the viewing application from acquire system that is executing on the image station 104. In an exemplary embodiment, the current window level and width setting in interactive review mode will be used to display the images in acquire mode. In addition, the image thickness will change to the acquired image thickness during acquire mode. However, if the user enters the interactive review menu 200 again, the system will display the image at the previously selected thickness value as depicted in the image thickness control 208.

The batch Rx button 224 shown in FIG. 2 allows the user to invoke another application that uses a batch mode of reformatting reconstructed images. Selecting the back button 226 results in the user exiting the interactive review screen 200 and entering a screen from the calling application that initiated the interactive review screen 200, while still maintaining an interactive review screen 200 in the background. As the interactive review screen 200 is exited, a button labeled "enter viewing application" will be displayed on a screen in the calling application to regain access to the interactive review screen 200. Selecting the quit button 228 causes the user to exit the current viewing application session and therefore all user settings associated with the current interactive review session will be reset.

In an exemplary embodiment, the viewport of the viewing application, displayed on the workstation 106, provides additional capabilities of entering user display input, user interval value input and user slice thickness input. The patient name in the viewport can be turned on or off by double clicking with a mouse on a patient name annotation field on the viewport. The display field of view (DFOV) can be increased and decreased using the left and right mouse buttons on a DFOV annotation field in the viewport. The image thickness can be adjusted using the left and right mouse buttons on an image thickness annotation field in the viewport. The image location can be changed by dragging the mouse across the image location field while holding down the left button on the mouse. The render mode can be changed using the dropdown menu option when the left mouse button is pressed on a render mode annotation field. The examples above are not meant to be exhaustive, but are given as illustrations of the types of capabilities that exist.

An embodiment of the present invention allows a user to display axial images at slice thicknesses and interval values other than what was natively prescribed. This can result in a user being able to visualize the entire exam in less time or in improved low contrast detectability. The ability to run the viewing application and reformat the reconstructed image before the scanning and reconstructing have been completed may allow a medical team to respond more quickly to a medical emergency. In addition, the ability to explicitly specify an interval value can result in more accurate and focused reviews of the reconstructed image by medical personnel. A reduction in filming and archiving costs may also result because of the capability to film and archive an axial image at an increased slice thickness.

Although the preceding embodiments are discussed with respect to medical imaging, it is understood that the image acquisition and processing methodology described herein is not limited to medical applications, but may be utilized in non-medical applications.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for managing axial images, the method comprising:
   receiving at least a portion of a reconstructed axial image, wherein said reconstructed axial image includes a preselected number of completed reconstructed slices, a slice thickness and an interval value;
   creating a reformatted axial image in response to said portion of said reconstructed axial image, wherein said creating includes:
   modifying said slice thickness in response to user slice thickness input;
   modifying a pixel intensity in response to a user render option input;
   updating said interval value in response to user interval value input; and
   displaying said reformatted axial image in response to user display input, said user display input comprises:
   an instruction to save a current view of said reformatted axial image in a secondary capture image format; and
   an annotation level selection including a full annotation level, a partial annotation level, a custom annotation level, and a none annotation levels, wherein the full annotation level displays a current acquisition status, a current reformat location, a current reformat thickness, a date, a patient name, and a hospital name.

2. The method of claim 1 wherein said user interval value input includes an explicit value for said interval value.

3. The method of claim 1 wherein said user slice thickness input includes an explicit value for said slice thickness.

4. The method of claim 1 further including:
   receiving at least one additional said completed reconstructed slice; and
   displaying said reformatted axial image in response to said user display input and to said additional completed reconstructed slice.

5. The method of claim 4 wherein said receiving at least one additional said completed reconstructed slice is performed in response to a user selecting a resume acquire button.

6. The method of claim 1 wherein said receiving, said creating and said displaying are performed in an interactive mode.

7. The method of claim 1 wherein said user display input includes a zoom option.

8. The method of claim 1 wherein said user display input includes an image location selection.

9. The method of claim 1 wherein said user display input includes a resize selection.

10. The method of claim 1 wherein said user display input includes a measurement selection.

11. The method of claim 1 wherein said user display input includes an instruction to save said reformatted axial image in a reformat format.

12. The method of claim 1 wherein said user slice thickness input includes an instruction to change said slice thickness by a pre-selected value.

13. The method of claim 1 wherein said user slice thickness input includes an instruction to set said slice thickness to a pre-selected value.

14. The method of claim 1 wherein said user interval value input includes an instruction to change said interval value by a pre-selected value.

15. The method of claim 1 wherein said user interval value input includes an instruction to set said interval value to a pre-selected value.

16. A method for managing axial images, the method comprising:

receiving a reconstructed axial image, wherein said reconstructed axial image includes a slice thickness and an interval value;

creating a reformatted axial image in response to said reconstructed axial image, wherein said creating includes:

modifying said slice thickness in response to user slice thickness input;

modifying a pixel intensity in response to a user render option input;

updating said interval value in response to user interval value input wherein said user interval value input includes an explicit value for said interval value; and displaying said reformatted axial image in response to user display input, said user display input comprises:

an instruction to save a current view of said reformatted axial image in a secondary capture image format; and an annotation level selection including a full annotation level, a partial annotation level, a custom annotation level, and a none annotation level, wherein the full annotation level displays a current acquisition status, a current reformat location, a current reformat thickness, a date, a patient name, and a hospital name.

* * * * *